United States Patent [19]

Havinga et al.

[11] 4,390,451
[45] Jun. 28, 1983

[54] CONCENTRATED AQUEOUS METAL ALDONATE AND/OR AMMONIUM ALDONATE COMPOSITION

[75] Inventors: Reginoldus Havinga, Schalkhaar; Reinder Torenbeek, Le Twello; Petrus H. M. Schreurs, Deventer, all of Netherlands

[73] Assignee: AKZO N.V., Arnhem, Netherlands

[21] Appl. No.: 274,250

[22] Filed: Jun. 16, 1981

[30] Foreign Application Priority Data

Jun. 30, 1980 [NL] Netherlands .......................... 8003771

[51] Int. Cl.$^3$ ............................................. B01J 13/00
[52] U.S. Cl. ............................... 252/311; 252/174.17; 252/174.19; 252/174.23
[58] Field of Search ............... 252/311, 174.17, 174.19, 252/174.23

[56] References Cited

U.S. PATENT DOCUMENTS

| | | | |
|---|---|---|---|
| 2,730,505 | 1/1956 | Jordan | 252/311 |
| 3,007,879 | 11/1961 | Jordan | 252/311 X |
| 3,146,200 | 8/1964 | Goldstein et al. | 252/311 X |
| 3,454,501 | 7/1969 | Ziffer et al. | 252/79.4 X |
| 3,998,761 | 12/1976 | Gary et al. | 252/174.23 X |

FOREIGN PATENT DOCUMENTS

| | | |
|---|---|---|
| 43161 | 9/1981 | European Pat. Off. . |
| 586371 | 10/1933 | Fed. Rep. of Germany . |
| A74975 | 4/1937 | Netherlands . |
| 7803143 | 10/1978 | Netherlands . |

OTHER PUBLICATIONS

Kirk-Othmer, Ency. of Chemical Tech. vol. 10 pp. 741–742.
Chemical Abstracts, vol. 91, 1979 (p. 522).

*Primary Examiner*—Lucille M. Phynes
*Attorney, Agent, or Firm*—Stevens, Davis, Miller & Mosher

[57] ABSTRACT

The present invention relates to a concentrated aqueous composition of metal aldonate and/or ammonium aldonate. Part of the aldonate is dissolved and part of it is suspended in the water. Sodium gluconate is preferred. The present composition should contain a colloidally dispersed gum as suspending agent. Gums containing carboxyl groups such as xanthan gum are particularly well suited for making the suspension. In this manner, stable compositions having a high aldonate content are obtained. The composition can be used in cleansing preparations for glass and metal surfaces, in solution for etching aluminum, in galvanizing processes, in the tanning of leather, in paper making, in treatment of textiles, in paint removers, fixing baths in photography, and in agricultural and pharmaceutical preparations.

15 Claims, No Drawings

CONCENTRATED AQUEOUS METAL ALDONATE AND/OR AMMONIUM ALDONATE COMPOSITION

This invention relates to an improved aqueous composition containing a metal aldonate and/or ammonium aldonate.

A composition of the type indicated above is disclosed in U.S. Pat. No. 3,454,501. It is known from this patent that it is a problem in actual practice to prepare stable concentrated aqueous solutions of aldonates economically, and, more particularly, gluconates. For instance, the solubility of sodium gluconate in water at 25° C. is only 37% (calculated on the weight of the total solution). Solutions having a higher concentration are unstable.

The problem is solved in accordance with U.S. Pat. No. 3,454,501 by preparing compositions containing both an aldonate and the corresponding aldonic acid. Thus, it is possible to prepare compositions of sodium gluconate and gluconic acid containing 50–90 peercent by weight of dissolved gluconate and gluconic acid. Such compositions can be obtained directly by mixing the various constituents. It is preferred, however, that these compositions should be prepared by fermentation, the fermentation medium being prepared first with only a portion of the aldose and the remainder of the aldose being added at a later stage of the fermentation process. The adonic acid formed is only partially neutralized.

The present invention provides a concentrated aqueous composition containing a metal aldonate and/or ammonium aldonate and characterized in that part of the aldonate is present in the dissolved state and part of it is in the suspended state and the composition contains a colloidally dissolved gum as suspending agent. The present compositions have several advantages over the solutions prepared by the process of the above-mentioned United States Patent. During transport and storage it may happen that the compositions are exposed to very low temperatures. The compositions according to the invention stand freeze-thaw cycles without being adversely affected. In the disclosed solutions, on the other hand, crystallization takes place at low temperatures (−10° C.). Consequently, thawing is not automatically followed by dissolving to form a stable solution. Moreover, after thawing and during renewed preparation of solutions care must be taken in order to obtain the same concentration. Further, the present solutions have a higher aldonate content per unit volume than the prior art solutions. This is of advantage with respect to transport and storage.

It should be added that where the action of the metal is of primary importance and not that of the aldonate, the presence of aldonic acid is superfluous and sometimes even bothersome. This is true for instance for the use of zinc gluconate, magnesium gluconate and iron gluconate in agriculture and for pharmaceutical purposes. The present compositions therefore have a wider field of application than the aldonic acid-containing solutions of the prior art.

Moreover, the aldonic acid-containing solutions have a pH lower than 6, whereas the pH of the composition of the invention is generally in the range of from 6 to 8. Consequently, the compositions provided by the invention are generally less corrosive, which may be of importance in view of possible attack of pipes, pumps and the like.

Finally, with certain uses the prior art solutions have the disadvantage that they must first be neutralized. This is desirable for instance if the compositions are to be applied as a retarding agent or plasticizer in working up cement and gypsum.

It is an object of the present invention to provide a concentrated aqueous composition which contains a metal aldonate or ammonium aldonate having improved storage and transport characteristics. Another object of the invention is to provide an aqueous solution containing an aldonate which is adapted to pass through freeze-thaw cycles without substantial change in concentration of aldonate solution in the composition. A still further object is to provide aqueous aldonate compositions which do not contain aldonic acid as an essential component, are less corrosive to metal and do not require neutralization prior to use as a retarding agent in cement based formulations.

The foregoing objects and others are accomplished in accordance with the invention by providing an aqueous composition which contains a metal aldonate or ammonium aldonate suspended in an aqueous solution thereof and a process for preparing the composition. The aqueous medium contains a gum colloid which serves as a suspending agent.

An essential characteristic of the present composition is that the aldonate is partly present in the dissolved and partly in the suspended state. As is known, the solubility of aldonates in water is relatively low. By suspending the aldonate in water, it is possible to obtain concentrations that are considerably beyond the solubility limit of the aldonate. This method permits varying the aldonate concentration between wide limits. The choice of the concentration partly depends on the use envisaged. It is preferred, however, that the present composition should contain at least 10 percent by weight and, preferably, from about 20 percent to about 60 percent by weight of aldonate in the suspended state.

By an "aldonate" as used herein is to be understood a salt of a polyhydroxycarboxylic acid formed upon oxidation of the aldehyde group of an aldose. Examples of aldonates include salts of gluconic acid, mannoic acid, gulonic acid, galactonic acid, arabonic acid, and glucoheptonic acid. The present composition may, of course, also contain mixtures of aldonates.

It is preferred that the composition according to the invention should contain a gluconate. Examples of suitable gluconates include sodium gluconate, potassium gluconate, ammonium gluconate, calcium gluconate, magnesium gluconate, zinc gluconate, cobalt gluconate, manganese gluconate, iron gluconate, and the like. In most cases use is made of sodium gluconate.

A second characteristic of the present composition is that it contains a colloidally dissolved gum. The presence of such a gum plays an essential role in keeping the aldonate particles in the suspended state.

By "gums" are to be understood any suitable substance which when dissolved or colloidally dispersed in water facilitates the preparation of a viscous solution or dispersion (see Kirk & Othmer, Encyclopedia of Chemical Technology, Second Edition, 1966, Vol. 10, pp. 741–742). Depending upon the aldonate and the concentration thereof the composition should contain 0.01–10% by weight of colloidally dissolved gum. Natural, modified natural, or synthetic gums may be used. By preference, the contemplated composition contains as suspending agent a carboxyl groups-containing gum. Examples thereof include natural gums such as guar, tamarind and tragacanth, modified gums such as xanthan gum and sodium carboxyl-methyl cellulose, synthetic gums such as carboxyvinyl polymers of the type marketed by Goodrich Tire and Rubber Co. under the trade mark "Carbopol" and poly(methylvinyl ether/-maleic anhydride of the type marketed by General Aniline Film (G.A.F.) Corporation under the trade mark "Gantrez AN."

The present composition may, of course, also contain mixtures of these suspending agents.

Of the above-mentioned suspending agents, xanthan gum is the one that is preferred. Generally about 0.05–5 percent by weight and preferably 0.1–0.5 percent by weight is incorporated in the composition. The compositions thus prepared display excellent stability and keeping properties.

The viscosity of the composition is dependent on the concentration of the aldonate, the size of the suspended particles and the choice and added amount of suspending agent.

It is possible in a simple manner to prepare pastes as well as pourable compositions. The option depends on the use envisaged.

Further, the composition may contain conventional additives, such as a biocide. As biocide it is preferred to employ formaldehyde in an amount of 0.01–1 percent by weight.

The present suspensions can be prepared in a known manner and with the aid of usual apparatus. For example, the suspensions may be prepared by mixing the suspending agent with the aldonate and subsequently suspending this mixture in water with stirring. Alternatively, the suspending agent may first be introduced into the water, followed by adding the aldonate, or the aldonate may be added as the first component. In all these processes the aldonate may be used in the solid state, dissolved, or in the form of a slurry.

The suspension also may be prepared by evaporating water from an aqueous solution of the aldonate, the suspending agent being added before, during or after evaporation.

As a rule, the suspension is prepared at a temperature of 15°–100° C.

The compositions provided by the invention may be used for many purposes, for example, for cleaning bottles or metal surfaces, etching of aluminum and in certain galvanizing processes, in the tanning of leather, in paper making, in the treatment of textiles, in removing paint, as a diluent in drilling fluids, in working up cement and gypsum, in fixing baths applied in photography, as a carrier of metals in agriculture and for pharmaceutical purposes.

Sodium gluconate suspensions are preferably used in detergents for bottles and metal surfaces, for instance, and as a retarding or plasticizing agent in working up cement or gypsum.

The following examples serve to further illustrate the invention.

EXAMPLE I

Each of the aqueous sodium gluconate compositions listed in Table 1 was prepared as described below.

Solutions of suspending agents colloidally dispersible in water were prepared at room temperature and with stirring (with the aid of an Ultra-Turrax Type T45 mixer). To these solutions, small portions of dry sodium gluconate were gradually added, with stirring.

When the polymer used was incompatible with a high content of dissolved sodium gluconate, formation of a slimy mass took place before the saturation point was reached.

To the solutions, however, that were compatible with sodium gluconate the addition of gluconate was continued until the resulting suspensions contained the sodium gluconate partly in the dissolved and partly in the suspended state. To avoid fungal growth 0.2% of a 37%-formaldehyde solution was added.

All these compositions were tested for stability by storing them at room temperature for four weeks and checking them for separation of a clear, transparent top layer. The compositions were rated as stable when they showed less than 2 ml of clear separation per 100 g of suspension. The various ingredients and the properties of the compositions thus prepared are given in Table 1.

TABLE 1

| Sample No. | wt. % Na gluconate | suspending agent compound | wt. % | properties of suspension |
|---|---|---|---|---|
| 1. | <40 | methyl cellulose (Henkel C 2006 K 25) | 2 | suspending agent precipitates |
| 2. | <40 | hydroxybutyl methyl cellulose (Methocel HB) | 0.7 | suspending agent precipitates |
| 3. | <40 | hydroxypropyl methyl cellulose (Methocel F 50) | 2 | suspending agent precipitates |
| 4. | <40 | hydroxypropyl cellulose (Klucel) | 0.7 | suspending agent precipitates |
| 5. | <40 | polyvinyl pyrrolidone (PVP K 15 G.A.F.) | 3.5 | suspending agent precipitates |
| 6. | <40 | polyvinyl alcohol (Mowiol 18-88) | 2 | suspending agent precipitates |
| 7. a | 70 | hydroxyethyl cellulose Natrosol 250 HHR) | 0.35 | suspending agent precipitates |
| b | | Natrosol 250 HR | 0.7 | suspending agent precipitates |
| c | | Natrosol 180 HHWR | 1 | suspending agent precipitates |
| 8. | 60 | xanthan gum (Rhodopol 23) | 0.2 | stable, pourable |
| 9. | 60 | xanthan gum (Rhodopol 23) | 0.5 | stable, paste |
| 10. | 70 | sodium salt carboxyvinyl polymer (Carbopol 934) | 0.3 | stable, pourable |
| 11. | 70 | sodium salt CMC (Akzo H 921) | 0.6 | stable, paste |
| 12. | 70 | interpolymer of methylvinyl ether and maleic anhydride (Gantrez AN 139) | 3 | stable, thin paste |
| 13. | 70 | guar gum | 0.5 | stable, paste |
| 14. | 70 | tamarind | 0.5 | stable, paste |
| 15. | 70 | xanthan gum (Rhodopol 23) | 0.15 | stable, pourable |
| 16. | 75 | xanthan gum (Rhodopol 23) | 0.15 | stable, paste |
| 17. | 83.3 | xanthan gum (Rhodopol 23) | 0.08 | stable, stiff paste |
| 18. | 86.6 | xanthan gum (Rhodopol 23) | 0.07 | stable, stiff paste |

Samples 1 through 7 are given for comparison. The suspending agents used in these experiments do not become colloidally dissolved in a sodium gluconate solution and consequently stable suspensions are not obtained. Samples 8–18 are suspensions provided by the invention. Since the solubility of sodium gluconate in water at 25° C. is only 37 percent by weight, these compositions contain a substantial amount of sodium gluconate in the suspended state, which however has no detrimental effect on the stability of the compositions.

The results also show that the viscosity of the compositions is influenced by the concentration of the gluconate and of the suspending agents.

EXAMPLE II 61.2 parts by weight of sodium glucoheptonate 2 aq, 38.65 parts by weight of a 30%-sodium glucoheptonate solution in water and 0.15 part by weight of xanthan gum (Rhodopol 23) were intimately mixed at room temperature (with the aid of an Ultra-Turrax type T45 mixer) until a homogeneous, thin, pourable paste was obtained containing 65% by weight of sodium glucoheptonate.

This suspension was kept at room temperature and displayed no separation after 4 weeks' storage at room temperature.

A suspension prepared in an identical manner, except that no xanthan gum was included, was found to result within 1 hour in about 4 ml clear separation per 100 g suspension.

EXAMPLE III

The gluconate compositions listed in Table 2 were prepared by using the following procedure:

At a room temperature and with stirring (using an Ultra-Turrax mixer of the T45 type) solutions were prepared of the colloidally water soluble polymers listed in the table. Gluconates of different metals were added to the colloidal suspensions and intimately mixed. The resulting suspensions were evaluated for their properties, as indicated in Table 2, and stored for 4 weeks at room temperature, after which they were evaluated for separation of clear liquid in the manner described in Example I.

All compositions were found to be stable. The various constituents and the properties of the compositions thus obtained are given in Table 2. On the basis of the solubility data provided in the table some idea is given about the amount of gluconate present in the suspended state.

TABLE 2

| M | content composition | solubility (wt. %) at 25° C. | compound | wt. % | properties |
|---|---|---|---|---|---|
| $Ca^{2+}$ | 24 | 3 | xanthan gum (Rhodopol 23) | 0.4 | fairly pourable |
| $Zn^{2+}$ | 23 | 10 | xanthan gum (Rhodopol 23) | 0.4 | fairly pourable |
| $Zn^{2+}$ | 23 | 10 | Na-CMC* (Akzo CMC H921) | 0.8 | soft paste |
| $Zn^{2+}$ | 23 | 10 | Na-salt carboxy vinyl polymer (Carbopol 934) | 0.8 | stiff paste |
| $Zn^{2+}$ | 31 | 10 | xanthan gum (Rhodopol 23) | 0.37 | stiff paste |
| $Mg^{2+}$ | 31 | 13 | Na-CMC* (Akzo CMC H921) | 0.75 | soft paste |
| $Mg^{2+}$ | 39 | 13 | xanthan gum (Rhodopol 23) | 0.35 | soft paste |
| $Co^{2+}$ | 37 | 16 | xanthan gum (Rhodopol 23) | 0.35 | soft paste |
| $Fe^{2+}$ | 46 | 7 | xanthan gum (Rhodopol 23) | 0.33 | pourable |
| $Fe^{2+}$ | 65 | 7 | xanthan gum (Rhodopol 23) | 0.3 | paste |
| $Mn^{2+}$ | 46 | 9 | xanthan gum (Rhodopol 23) | 0.33 | pourable |
| $Mn^{2+}$ | 69 | 9 | xanthan gum (Rhodopol 23) | 0.3 | pourable |
| $K^+$ | 66 | 51 | xanthan gum (Rhodopol 23) | 0.3 | pourable |

*sodium carboxy-methyl cellulose

The above results show that stable suspensions can be prepared with gluconate salts other than sodium gluconate.

EXAMPLE IV 2.25 g of xanthan gum (Rhodopol 23) were suspended in 445 ml of water with the aid of an Ultra-Turrax mixer (Type T45). After the composition had been allowed to stand for 30 minutes, 1050 g of dry sodium gluconate were added with renewed stirring. Stirring was continued for 5 minutes. The temperature of the resulting suspension was 45° C. To the composition there were added 3 g of a 37% formaldehyde solution.

The next day the suspension was de-aerated in vacuo. The density of the suspension was 1.430 kg/m³.

Subsequently, part of the suspension was stored for 56 days at 20° C., and over the same period another part was stored at 30° C. After 28 and 56 days it was determined how much clear liquid had separated off. For the suspension kept at 20° C. the amounts were 0.5 and 3.0 ml/500 g, respectively, and for the suspension stored at 30° C. the amounts were 3.0 and 7.0 ml/500 g suspension. These data demonstrate that the present compositions have good storage stability. Moreover, after 56 days no fungal growth could be observed.

EXAMPLE V 2.25 g of xanthan gum (Rhodopal 23) were suspended in 645 g of a 30%-sodium gluconate solutions with the aid of an Ultra-Turrax (T45 type) mixer. After the composition had been allowed to stand for 30 minutes, 855 g of dry sodium gluconate were added, with stirring. Next, part of the composition was stored for 56 days at 20° C. and over the same period another part was kept at 30° C. After 56 days it was determined how much clear liquid had separated off. For the suspension kept at 20° C. the amount was found to be nil and for the composition stored at 30° C. it was found to be 0.5 ml/500 g. These results confirm that the present compositions have excellent storage stability.

EXAMPLE VI

A slurry which contained 60 percent by weight of sodium gluconate was homogenized with the aid of a T45 type Ultra-Turrax mixer. To 2000 g of this slurry were added, over a period of 2 minutes and with stirring, 4 g of xanthan gum (Rhodopol 23). After the composition had been allowed to stand for 30 minutes, 670 g of dry sodium gluconate were stirred into it. Subsequently, part of the suspension was stored for 56 days at 20° C. and over the same period another part was kept at 30° C.

After 56 days the amounts that had separated off were 0.5 and 1.5 ml/500 g, respectively. These data confirm the results of Examples IV and V.

Although the invention has been described in detail for the purpose of illustration, it is to be understood that such detail is solely for that purpose and modifications can be made therein by those skilled in the art without departing from the spirit and scope of the invention except as it may be limited by the claims.

What is claimed is:

1. A concentrated aqueous composition, comprising
   an aldonate of at least one member selected from the group consisting of a metal aldonate and an ammonium aldonate, part of said aldonate being present in a dissolved state and part of said aldonate being present in a suspended state; and
   a colloidal gum suspending agent.
2. The composition according to claim 1, containing at least 10 percent by weight of suspended aldonate.
3. The composition of claim 1, containing 20–60 percent by weight of suspended aldonate.
4. The composition of claim 1, 2 or 3, wherein the aldonate is a gluconate.
5. The composition of claim 4 wherein the aldonate is sodium gluconate.
6. The composition of claim 4, wherein the composition comprises a gum having carboxyl groups as suspending agent.
7. The composition of claim 5, wherein the aldonate is sodium gluconate and the gum contains carboxyl groups.
8. The composition of claim 6 or claim 7 wherein the suspending agent is xanthan gum.
9. The composition of claim 6 or claim 7, further comprising a biocide.
10. The composition of claim 9, wherein the biocide is formaldehyde.
11. A substantially stable aqueous suspension comprising an aldonate in solution, a colloidal gum suspending agent, and an aldonate suspended in the solution.
12. A process for preparing a substantially stable saturated aqueous solution containing suspended aldonate which comprises stirring in water containing a colloidal gum suspending agent an aldonate in an amount exceeding the solubility of the aldonate in water at the temperature of the water until a saturated solution of aldonate having undissolved aldonate suspended therein is obtained.
13. The process of claim 12 wherein the aldonate is a gluconate, the temperature of the water is from about 15° C. to about 100° C. and 0.05 to 5 percent by weight of a gum having carboxyl groups is mixed with the aldonate and water as a suspending agent.
14. The process of claim 13 wherein a biocide is included in the suspension.
15. A suspension saturated with a metal aldonate or an ammonium aldonate solute, having undissolved metal aldonate or ammonium aldonate substantially uniformly suspended therein and a pH of at least 6.

* * * * *